United States Patent [19]

Ritano

[11] Patent Number: 4,971,556
[45] Date of Patent: Nov. 20, 1990

[54] ENDODONTISTRY BIT SET

[76] Inventor: Francesco Ritano, Via S.Giovanni Bosco, 11, Soverato (Catanzaro), Italy, 88068

[21] Appl. No.: 216,786

[22] Filed: Jul. 8, 1988

[30] Foreign Application Priority Data

Jul. 10, 1987 [IT] Italy ............................... 48172 A/87

[51] Int. Cl.$^5$ ................................................ A61C 5/02
[52] U.S. Cl. ................................................... 433/102
[58] Field of Search ....................... 433/102, 165, 224

[56] References Cited

U.S. PATENT DOCUMENTS 4,518,356  5/1985  Green ................................... 433/102
4,836,780  6/1989  Buchanan ............................. 433/102

FOREIGN PATENT DOCUMENTS 2022475 12/1979 United Kingdom ................ 433/102

Primary Examiner—Cary E. Stone
Attorney, Agent, or Firm—Thomas R. Vigil

[57] ABSTRACT

The pulp canal of a tooth requiring filling is hollowed out using boring bits fitted to and driven by a vibrating instrument; the bits are organized in sets, with a number of discrete sets making up the full range. The abrasive tine of the bits of each set is tapered; its length and tip diameter remain the same throughout the set, whereas the diameter at the point where it joins with the shank increases progressively from the smallest to the largest size.

8 Claims, 1 Drawing Sheet

ENDODONTISTRY BIT SET

BACKGROUND OF THE INVENTION

The invention relates to the operation of hollowing out the pulp canals of teeth, utilizing endodontistry instruments of the type consisting in a boring bit fitted to a vibrating handgrip; such a grip may be of a type capable of transmitting sonic or ultrasonic vibratory motion to the bit fitted, or may be purely mechanical, but at all events, will be designed to vibrate the bit rather than investing it purely with rotary motion in conventional manner.

With vibration thus transmitted from the grip to the bit in combination with suitable fluids supplied either previously or simultaneously to the cavity of the tooth, the pulp is dissolved, and a microscopic break-up in the dentine of the canal wall is brought about; in this way, the pulp canal is hollowed out in readiness for filling.

With the advent of vibrating instruments, it has become clear that conventional drilling bits are not able to exploit vibratory motion to full advantage.

In effect, conventional instruments utilize a type of bit exhibiting a shape and a cutting surface best suited to vertical filing and/or rotary action, whether manually or mechanically induced, which are movements that hitherto have typified the method of removing pulp from a tooth to be filled. FIG. 1 of the accompanying drawings shows the schematic representation of a conventional bit; this is flanked by a tabulated summary of the principal specifications and standard diameters currently in use, which are to ISO. In the table, D1, D2 and D3 denote the diameter, in mm, of each corresponding section of the bit, the working tine portion PO of which measures 16 mm from end to end. In the same table, "N. norm" denotes a standard reference number for the relative conventional bit, which reflects the tip diameter D1 expressed in 100ths of one mm.

With the introduction of vibrating endodontistry instruments, it has been observed that the vibratory motion transmitted by the grip is more pronounced in the more flexible part of the tine, in other words, the part that fans out when in operation to assume the shape of a cone (see FIG. 2), the base of which coincides with its tip.

The base diameter of the vibrating cone shape in question can be adjusted, by way of a special device incorporated into the grip, to give an oscillatory excursion of between 1 and 1.5 mm. Thus it happens that the base diameter of the cone can blanket any tip diameter across the entire range of conventional bits (see table, FIG. 1), and as a result, one of the essential features of these bits, namely, the fact of their increasing in tip diameter from one size to the next, is set at nothing.

The use of a set of conventional vibrating bits, increasing them progressively in size to the end of enlarging the cavity, is accompanied by a similarly progressive increase in the risk of the pulp canal becoming ovalized, of laceration, and of drift from the position of the apical extremities, which are impossible to assess exactly beforehand in vivo. by the same token, the passage from one size of bit to the next dictates an increase in rigidity of the tine, and with it, the impossibility of successfully following the curvilinear anatomy of the canal.

Finally, the vibratory motion which projects the bit sideways against the dentine wall of the pulp canal gives rise to the need for abrading surfaces different from those designed for the manually or mechanically induced linear or rotary movement of conventional instruments.

Accordingly, the object of the invention is to overcome the limitations and eliminate the drawbacks mentioned above, by setting forth a set of specially designed bits for endodontistry instruments, which are able to exploit the operating characteristics of a vibrating grip to the full.

SUMMARY OF THE INVENTION

The stated object is realized with a set of at least three endodontistry instrument bits according to the invention. Each such bit exhibits a tine that extends from the tip to a section at which it joins with a shank, fitted to the grip, and is tapered through its entire length.

The tip diameter of all the bits of the set remains identical, whereas the diameter of the join between tine and shank increases progressively from the smallest to the largest; similarly, the tines of all the bits of one set are identical in length, and the abrading surface extends along the entire length of the tine.

Certain notable advantages are obtained using a set of endodontistry bits according to the invention in conjunction with a vibrator type instrument grip, namely:

tip end flexibility remains constant in all bits of the set, so that all the tines fan out into a cone of constantly repeated dimensions and shape;

the effect of a progressive increase in diameter of the join between tine and shank is to produce a corresponding increase, from one bit to the next, of the degree of contact between the tine and the wall of the pulp canal, particularly through the first two thirds of the tine; accordingly, the efficiency of the boring action along these first two thirds (the widest section of the canal) is equal to that of the cone generated at the tip:

the entire length of a given pulp canal can be worked with each bit of the set according to the invention, so that one dispenses with the need for depth stops such as the washers that are utilized conventionally;

using a set of bits as disclosed, the dentist can either bore out from the root, departing from the apical extremity, or penetrate down toward the root from the top of the pulp chamber.

BRIEF DESCRIPTION OF THE DRAWINGS

The invention will now be described in detail, by way of example, with the aid of the accompanying drawings, in which.

DESCRIPTION OF THE PREFERRED EMBODIMENTS

According to the present invention, 10, 20 and 30 denote a set of three boring bits for use with an endodontistry instrument; the operative part, or tine PO, is of identical length in all three, and extends in a constantly tapering profile from the tip P to a section S where it joins with a shank G, which is held in the grip of the instrument.

The diameter D11 of the tip of each bit of the set remains the same, whereas the diameter of the join S between tine and shank increases in diameter viz, D31, D32 and D33 from the first bit 10 of the set to the last 30.

More exactly, the tip diameter D11 will be of an order between 0.8 and 0.15 mm, which takes account of the normal adjustment in vibration amplitude at the tip as permitted by the grip, of the need to guard against the risk of ovalizing or boring completely though the apical extremity, and of keeping maximum obtainable flexibility at the tip end of the tine.

The abrading surface of all the bits of the set extends the full length of the tine PO, and will be embodied to best advantage as a plurality either of projecting elements or of continuous ribs, the sharp edges of which are set at right angles to the axis of the bit itself; thus, the vibrator action is well exploited, with the edges striking against the pulp canal walls and removing the dentine in microscopic particles.

Notwithstanding the set illustrated consists of three bits, it is clear enough that any given number of bits can make up a set, the difference existing only in the diametral increment of the join S, from one size to the next.

Figure 1:
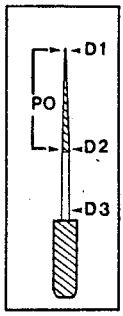
FIG. 1 is a table showing the ISO standard dimensions of conventional endodontistry instrument bits.
Figure 2:
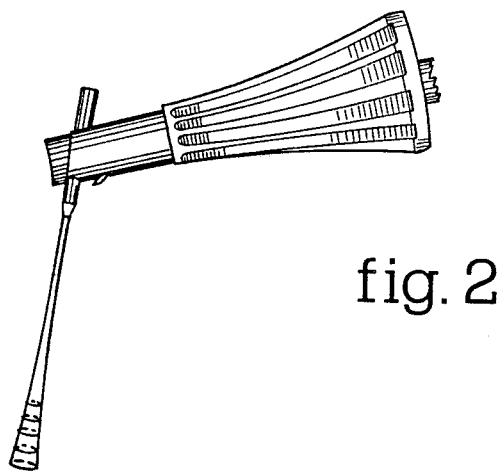
FIG. 2 illustrates the cone configuration generated in a bit fitted to and vibrated by the grip of the endodontistry instrument.
Figure 3:
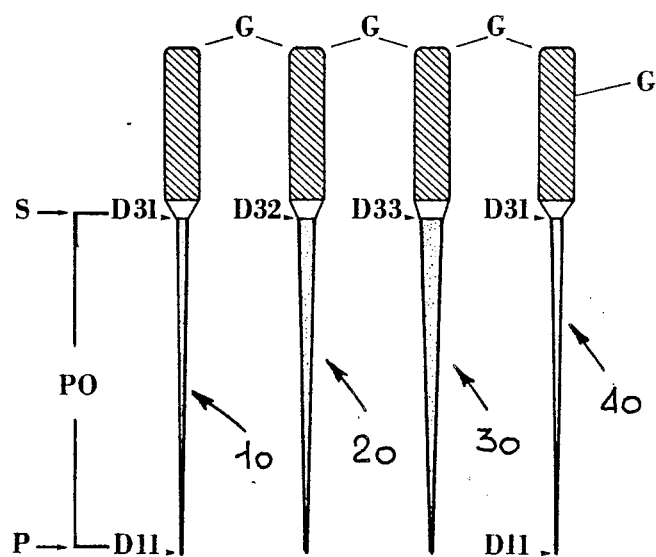
FIG. 3 illustrates a set of bits according to the invention.

According to the invention, the set of bits will advantageously include a further bit, denoted 40 in FIG. 3, which exhibits all the features described above except for the fact that the operative part, or tine PO, is completely smooth, and the diameter at its join S with the shank is identical to that of the smallest bit of the set —i .e D31.

The additional bit 40 in question permits of exploiting the vibrated cone configuration to spread and compress the filling material uniformly over and against the hollowed-out canal wall.

Likewise to advantage, it is envisaged that the dentist will make use of a number of sets of the endodontistry bits according to the invention, each one of which responds in all aspects to the above description, i.e. consisting in several bits with tines PO identical in length, but differs from the other sets precisely in the length of the tine PO. More exactly, the length of the tine exhibited by the bits of the several sets will be between 16 and 30 mm, a range which will effectively take in any length of pulp canal, either encountered in practice or estimated for operational purposes.

In a preferred embodiment, each set of the full range will comprise bits with a tine length 1 mm greater or less than that of the next shorter or longer size.

Thus, with a full range of endodontistry bits according to the invention, the dentist can select a bit of given length to suit the depth of the canal encountered, or to suit the succession of boring passes envisaged; the bits can be utilized set by set in sequence, or individually and at random, as best suits the inward or outward progression adopted in preparing the tooth.

It will be seen that, to possess the facility of selecting a bit of length corresponding to the depth of the pulp canal, or to a given required depth, signifies being free to dispense entirely with any form of depth stop of the type which is slid along the shank of the bit so as to limit penetration, as in conventional instruments. Accordingly, maneuvers can be effected with greater sureness, and one is able to eliminate an operation that is as fussy and inaccurate as it is damaging, not only by reason of the fact that an instrument subject to vibration causes the depth stop to slip away from its correct position, but also, because the depth stop itself prevents cutting fluid from flowing efficiently along the tine to the work area when in operation.

What is claimed:

1. A set of at least three endodontistry bits which are used in preparing and filling pulp canals and which are adapted for fitment to the handgrip of a sonically, ultrasonically or mechanically vibrated instrument, each bit comprising:

a tine, extending from the tip to a section at which it joins with a shank that is sized for fitment to the vibrating grip, said tine exhibiting a constant taper and a length measurement common to all the bits of the set and having means of abrasion that occupy its entire surface;

each of the tines in said set having the same tip diameter, common to all the bits of the set, which measures between 0.08 and 0.15 mm.;

a diameter at the joint between the tine and the shank which increases progressively from the smallest to the largest size bit of the set;

an additional bit, namely, a filling bit, with a tine extending from the tip to a section at which it joins with a shank that is sized for fitment to the vibrating grip, said tine exhibiting a constant taper, a length and tip diameter common to all the bits of the set, and a diameter at the joint with the shank identical to that exhibited by the smallest bit of the set, and said tine having a smooth surface and being utilized to apply the material used to fill a pulp canal hollowed out with the remaining bits of the set.

2. A group of several of the sets of endodontistry bits as defined in claim 1, wherein a single set comprises a given number of bits with tines of equal length but different from the length of the tines of the remaining sets, and wherein the length of any bit in the entire group measures between 16 and 30 millimeters.

3. A group of several sets of endodontistry bits as defined in claim 1 wherein a single set comprises a given number of bits with the tines of said bits having a length 1 mm greater or less than that of the next shorter or longer size bits in the other sets.

4. A set of at least three endodontistry bits which are used in preparing and filling pulp canals and which are adapted for fitment to the handgrip of a sonically, ultrasonically or mechanically vibrated instrument, each bit comprising:

a tine, extending from a tip to a section at which it joins with a shank that is sized for fitment to the vibrating grip, said tine exhibiting a constant taper and length measurement common to all the bits of the set and having means of abrasion that occupy its entire surface;

each tine in said set having the same tip diameter, common to all the bits of the set, which measures between 0.08 and 0.15 mm;

a diameter at the joint between the tine and the shank which increases progressively from the smallest to the largest size bit of the set; and, an additional filling bit with a tine extending from a tip to a section at which it joins with a shank that is sized for fitment to the handgrip, said filling bit tine exhibiting a constant taper, a length measurement and tip diameter common to all the bits of the set, and having a diameter at the joint with the shank identical to that exhibited by the smallest bit of the set, and said filling bit having a smooth surface and being utilized to apply or compact the material used to fill a pulp canal hollowed out with the remaining bits of the set.

5. An endodontistry instrument bit set, wherein each of said bits comprises a shank and a uniformly tapered tine having a tip, the improvement in which: each of said tines is of the same length from said tip to said shank; each of said tines has the same diameter tip; the respective diameter at the joint between the tine and the shank increases progressively from the smallest to the largest bit in said set; and, the set including at least one filling bit which is identical to the other bits except that in said filling bit, said tine has a smooth surface from tip to shank, and the diameter of the joint between the shank and the tine of the filling bit is the same as the corresponding diameter of the smallest bit in the set.

6. The endodontistry bit set of claim 5 in which each tine has an abrasive surface from tip to shank.

7. A method of operating an endodontistry instrument for abrading pulp in a pulp canal, said method comprising the steps of: successively attaching to said instrument respective endodontistry bits in a set of such bits, beginning with the smallest of said bits and progressing through the set to end with the largest of said bits in said set, each of said bits in said set having a shank and a tine which has a tip, and in which said tine is of the same length and of identical tip diameter, said tip diameter being between 0.08 and 0.15 mm., and in which each tine has a diameter at the joint between the tine and the shank which increases progressively from the smallest to the largest size bit of the set of: and providing vibratory motion to each of said bits through said instrument for generating a cone-shaped region through which said tine moves, the tip defining the base of said cone and said vibratory motion being provided while each of said bits extends into the canal.

8. A method of operating an endodontistry instrument for abrading pulp in a pulp canal, said method comprising the steps of: providing a set of endodontistry bits, each of said bits having a shank and a tine which has a tip, and wherein each respective tine in said set is of equal length and of identical tip diameter, said set of bits being further defined to provide respective tines of increasing joint diameter of each tine at the joint of that tine with said shank; conducting a plurality of pulp abrasion steps, each of said steps taking place sequentially, in a sequence starting with the use of a respective bit with a tine having the smallest of said joint diameters; using each successively larger bit, until the use of a bit with the tine with the largest of said joint diameters; each of said steps comprising: attaching to said instrument a respective bit, without any depth gauges attached thereto; and providing vibratory motion to said bit through said instrument for generating a cone-shaped region through which said tine moves, the tip defining the base of the cone shape and said vibratory motion being provided while each of said respective bits extends into the canal.

* * * * *

UNITED STATES PATENT AND TRADEMARK OFFICE
CERTIFICATE OF CORRECTION

PATENT NO. : 4,971,556

DATED : November 20, 1990

INVENTOR(S) : Francesco Riitano

It is certified that error appears in the above-identified patent and that said Letters Patent is hereby corrected as shown below:

On the title page, Item [19], should read --Riitano--.
            Item [76],"Inventor : Francesco Ritano" should read
                    --Francesco Riitano--.

Column 1, line 61 "by" should be --by--.

Signed and Sealed this

Sixth Day of April, 1993

*Attest:*

STEPHEN G. KUNIN

*Attesting Officer*    *Acting Commissioner of Patents and Trademarks*